(12) United States Patent
Cordaro

(10) Patent No.: US 7,160,301 B2
(45) Date of Patent: Jan. 9, 2007

(54) TRANSVERSE CONNECTOR SYSTEM

(75) Inventor: Nicholas M. Cordaro, Oceanside, CA (US)

(73) Assignee: SeaSpine, Inc., Vista, CA (US)

( * ) Notice: Subject to any disclaimer, the term of this patent is extended or adjusted under 35 U.S.C. 154(b) by 61 days.

(21) Appl. No.: 10/877,667

(22) Filed: Jun. 24, 2004

(65) Prior Publication Data
US 2005/0010222 A1  Jan. 13, 2005

Related U.S. Application Data

(60) Provisional application No. 60/483,947, filed on Jul. 1, 2003.

(51) Int. Cl.
A61B 17/70 (2006.01)

(52) U.S. Cl. .................................. 606/61

(58) Field of Classification Search ......... 606/FOR. 61
See application file for complete search history.

(56) References Cited

U.S. PATENT DOCUMENTS

| 5,261,907 | A | 11/1993 | Vignaud et al. |
| 5,522,816 | A | 6/1996 | Dinello et al. |
| 5,601,554 | A | 2/1997 | Howland et al. |
| 5,624,442 | A | 4/1997 | Mellinger et al. |
| 5,716,355 | A | 2/1998 | Jackson et al. |
| 5,752,955 | A | 5/1998 | Errico |
| 5,947,966 | A | 9/1999 | Drewry et al. |
| 5,980,523 | A | 11/1999 | Jackson |
| 6,113,600 | A | 9/2000 | Drummond et al. |
| 6,136,003 | A | 10/2000 | Hoeck et al. |
| 6,217,578 | B1 | 4/2001 | Crozet et al. |
| 6,283,967 | B1* | 9/2001 | Troxell et al. ............... 606/61 |
| 6,413,258 | B1* | 7/2002 | Bernhardt, Jr. ............. 606/61 |
| 6,554,832 | B1 | 4/2003 | Shluzas |
| 2003/0114853 | A1* | 6/2003 | Burgess et al. ............... 606/61 |

* cited by examiner

Primary Examiner—David H. Willse
(74) Attorney, Agent, or Firm—Harold L. Jackson

(57) ABSTRACT

A transverse connector system for interconnecting two spinal rods includes a connector arranged to span the distance between the rods with a rod receiving recess and a pin receiving bore on each end. A pin member such as a set screw is deposited within each bore with an enlarged head protruding from the bottom of the connector so that when the set screw is retracted into the bore the head engages a side of the respective rod to clamp the rod within the recess. The connector may comprise two elongated members with a recess and pin receiving bore at one end of each member, a middle coupler which allows three degrees of freedom between the members to accommodate any anticipated spatial orientation between the members and a set screw for securing the other ends of the members together.

19 Claims, 8 Drawing Sheets

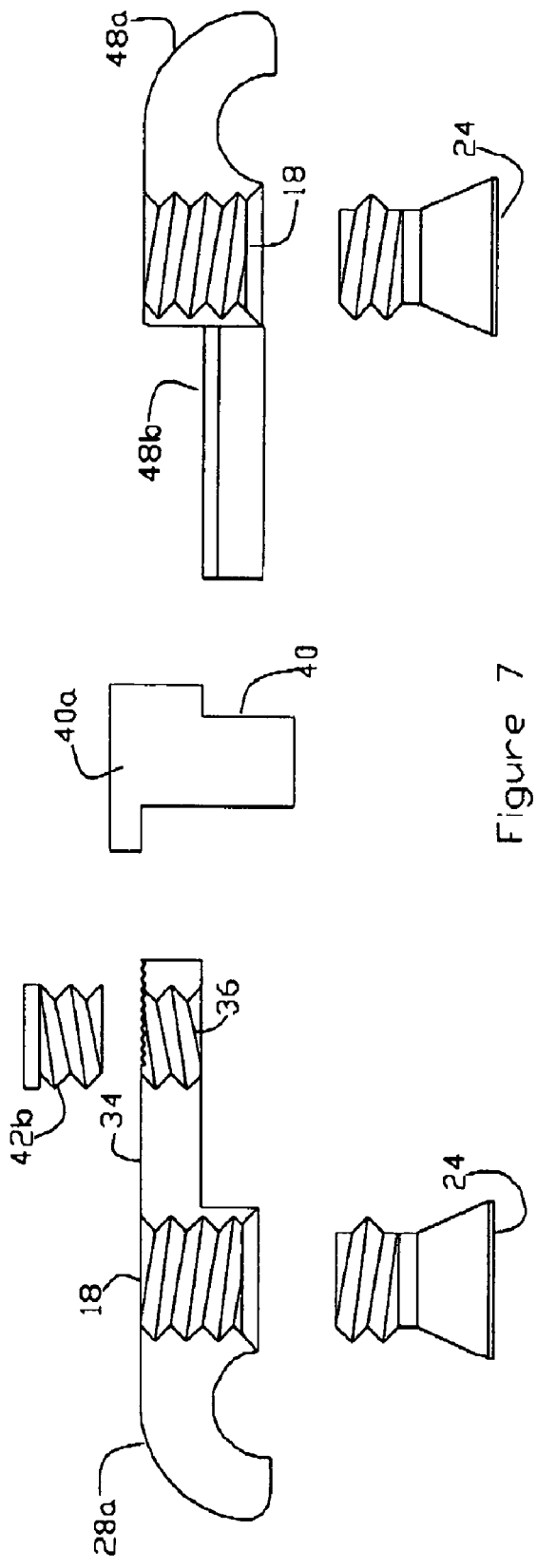
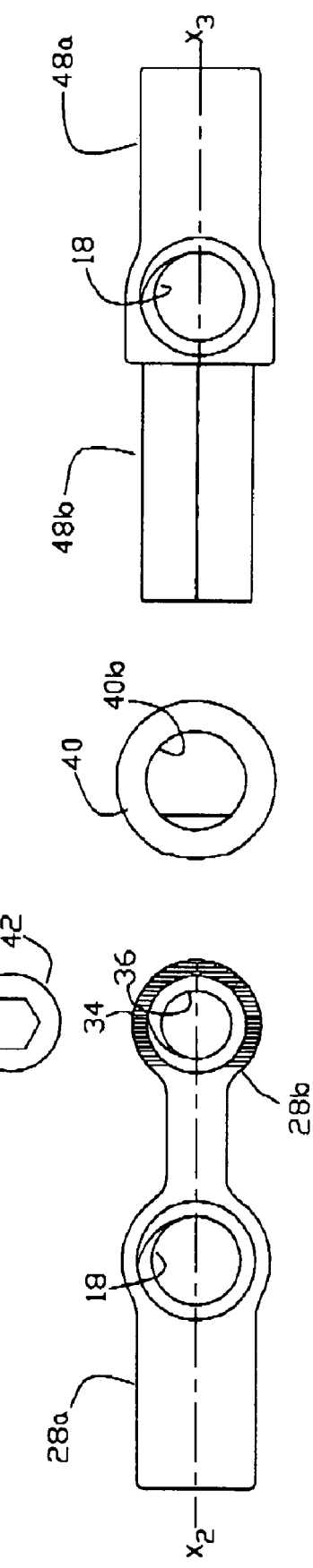
Figure 7
Figure 8

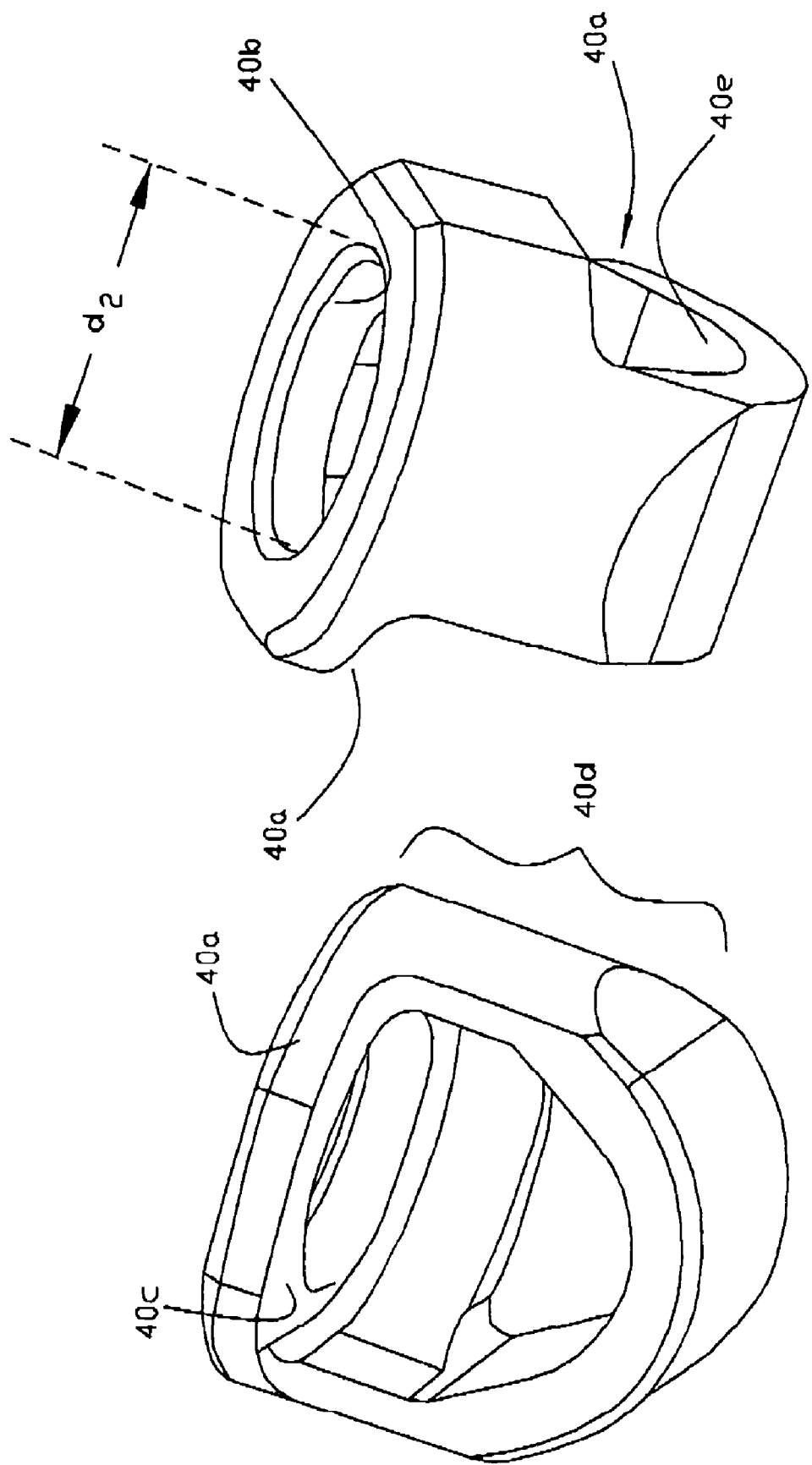

TRANSVERSE CONNECTOR SYSTEM

RELATED APPLICATION

This application is based on and claims priority of Provisional Application No. 60/483,947, filed Jul. 1, 2003, entitled Variable Transverse Connector for all common subject matter.

FIELD OF THE INVENTION

The present invention relates to a transverse connector system for interconnecting spinal rods that retain vertebrae in a fixed position. Another aspect of the invention is directed to a transverse connector system which is readily adjustable to join spinal rods of differing spatial orientations.

DESCRIPTION OF THE PRIOR ART

Numerous techniques have been employed to rigidly connect a pair of spinal rods for facilitating spinal fusion. A transverse connector system including one or more longitudinal members adapted to span the distance between two spinal rods along with a means for securing the end or ends of longitudinal member(s) to the spinal rods is generally used.

For example, see U.S. Pat. No. 5,522,816 ("'816 patent") issued to Dinello et al which discloses an elongated plate extending between a pair of hooks which are clamped to the respective rods by set screws. The set screws are positioned at a right angle to and extendable from the top surface of the respective hook with a portion of the hook extending completely underneath the spinal rod. This concept is disadvantageous in the clinical setting because bone or soft tissue protruding up to the lower surface of the spinal rod may restrict the ability of the surgeon in placing the lower hook portion underneath the spinal rod. U.S. Pat. No. 5,624,442 ("'442 patent") to Mellinger et al discloses a transverse connector rod clamping hook arrangement similar to the '816 hook configuration in that a portion of the hook is designed to extend under the rod.

U.S. Pat. No. 6,113,600, issued to Drummond et al, discloses a transverse connector which, to an extent, overcomes the problem associated with the '816 patent by positioning the set screws at an oblique angle relative to the longitudinal axis of the connector. This allowed for less of the rod engaging portion to extend underneath and around the spinal rod, slightly increasing the clinical usability. However, a clinical disadvantage of the '600 device is that the tightening mechanism is designed to extended parallel to the set screw, at the same oblique angle. A deep and narrow surgical wound site greatly limits the angle at which an instrument may protrude resulting in the probability that increased soft tissue retraction and/or dissection may be required.

The current invention provides the advantages of functioning properly with bone or soft tissue extending completely up to the bottom surface of the spinal rod and accommodating simple instrumentation that extends directly out of the wound site without additional soft tissue retraction or dissection.

With respect to transverse connector systems designed to accommodate differing spatial orientations of the spinal rods see U.S. Pat. No. 5,980,523 (Jackson); U.S. Pat. No. 6,217,578 (Crozet et al); and 6,544,832 (Shulzas). All three patents disclose transverse connector systems including elongated members extending between the rods that allow for three degrees of freedom between the members, i.e., translational, rotational and pivotal movement.

To accommodate the three degrees of freedom, the Jackson connector system requires a hooked end element secured to each rod via a set screw, a separate linking element positioned between the end elements and two screws to secure the separate linking element to the hooked end elements. This arrangement requires, not only the additional linking element, but requires the surgeon to tighten four screws to secure the rods in the desired position.

The Crozet et al cross connector system employs a pivot element positioned between hook elements anchored to the spinal rods via set screws with the pivot element being secured to one end of one of the hook elements by means of a threaded shaft and a hex nut. This arrangement requires the use of two separate tools (one for the set screws and one for the nut) to secure the rods in the desired orientation. In addition, the nut tightening tool may disturb the tissue surrounding the nut during the tightening procedure at best or at worst may be deflected by the nut into adjacent vertebrae in the event that the tool slips off of the nut.

Blackstone Medical Inc., of Springfield, Mass., has introduced a transverse connector system capable of accommodating common spatial orientation of spinal rods in which an external hex nut, rounded along the top edges, apparently to reduce tissue abrasion, is used to lock the connector elements together. This type of nut has the same disadvantages as the Crozet et al nut.

The Shulzas transverse connector system employs two elongated members with each member clamped at the first end to a respective rod. The second end of one of the members is in the form of a shaft which extends through a ball joint positioned in a truncated opening in the second end of the other member. The member having the truncated opening not only necessarily has a considerable width, but would be relatively expensive to manufacture. It is to be noted that Jackson, Crozet et al and Shulzas connectors all suffer from the use of rod clamping set screws which are oriented at an oblique angle to the longitudinal axis of the connector.

There is a need for a transverse connector system which overcomes the above disadvantages.

SUMMARY OF THE INVENTION

A transverse connector system for interconnecting two spinal rods in accordance with the present invention includes a connector, formed of one or more elongated members, adapted to span the distance between the rods. The connector has a rod receiving recess or groove on each end and a pin receiving bore adjacent each recess. A pin member, such as a set screw, is positioned within each pin receiving bore with the pins being arranged to be retracted within their associated bores to clamp the rods within the recesses and rigidly join the rods to the connector assembly. Preferably the pins are set screws with enlarged heads having beveled sides extending below the pin receiving bores so that the beveled sides, which may be straight or concave, engage the side of the rods to clamp the rods within the respective recesses. To simplify the installation procedure the set screws and pin receiving bores are preferably reverse threaded to accommodate clockwise rotation for the tightening procedure.

To facilitate the installation of the system while accommodating a reasonable spatial orientation of the spinal rods, the connector may be formed of first and second elongated members, a middle coupler and a locking screw. Each elongated member defines a longitudinal axis, a rod receiving groove on a proximal end thereof and a pin receiving bore adjacent the groove. A clamping pin is disposed in each pin receiving bore for securing the proximal end of the members to a respective rod. The distal end of the first member is provided with a threaded locking screw receiving bore. A ring coupler is mounted over the distal end of the first member for limited pivotal movement about an axis perpendicular to the longitudinal axis of that member. The coupler has an upper section with a cylindrical opening therein positioned over the locking screw receiving opening and a lower section of the coupler defines an internal curved surface through which the distal end of the second member extends to allow the second member to move along and rotate about its longitudinal axis relative to the first member. A locking screw threaded into the locking screw receiving bore in the coupler is arranged, when tightened, to lock the distal ends of the first and second members and the coupler together to maintain the spinal rods in the desired spatial orientation.

The present invention, as to its construction and function, may best be understood by reference to the accompanying description taken in conjunction with the appended drawings.

BRIEF DESCRIPTION OF THE DRAWINGS

FIG. 7 is a side elevational view of the disassembled connector system of FIG. 6;

FIG. 8 is a top plan view of the disassembled connected system of FIG. 6 minus the locking screws;

FIGS. 10 and 11 are different perspective views of the coupler of the system of FIG. 6.

DESCRIPTION OF THE PREFERRED EMBODIMENT

Figure 1:
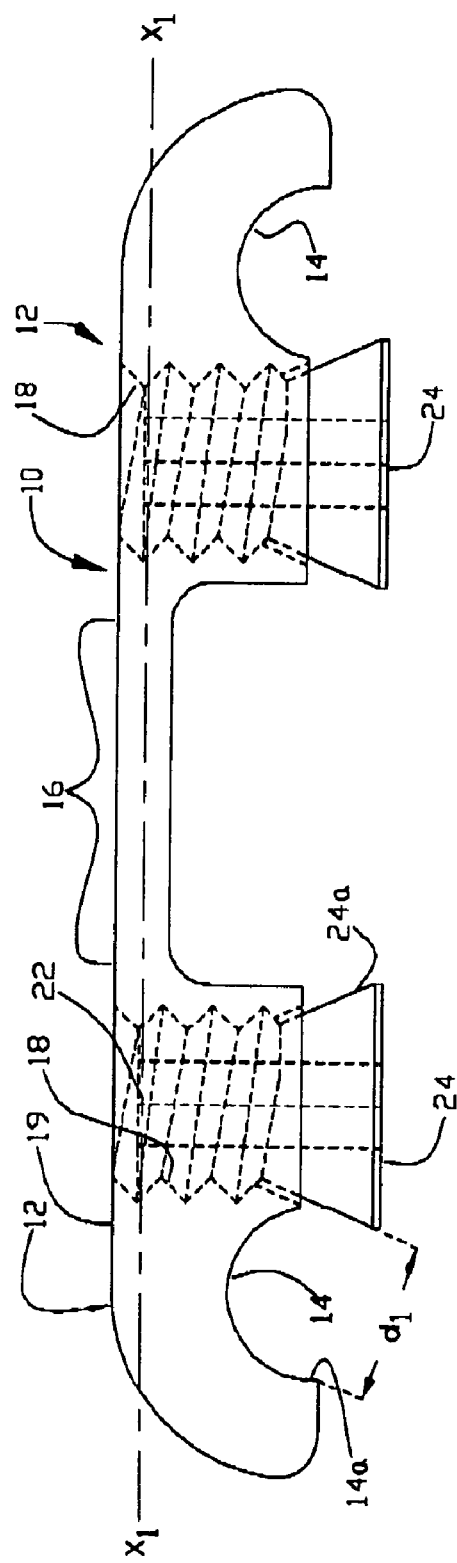
FIG. 1 is a side elevational view of a transverse connector system in accordance with the present invention wherein the connector is formed of a single unitary element.
Figure 2:
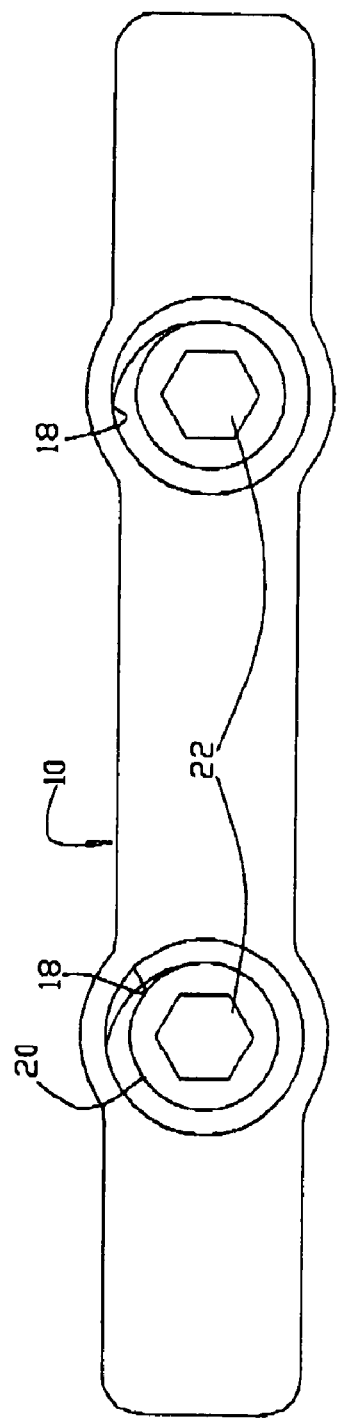
FIG. 2 is a top plan view of the connector system of FIG. 1.

Referring now to FIGS. 1 and 2 an elongated unitary connector 10 is arranged to span the distance between two spinal rods. The connector is formed with end sections 12 defining rod receiving surfaces, grooves or recesses 14 and an intermediate bridge section 16. A threaded clamping pin, e.g., set screw, receiving bore 18 is located adjacent each groove 14 and extends at a right angle to the top surface 19 and the longitudinal axis $X_1$ of the member 10 as illustrated. This arrangement overcomes the problems associated with prior art spinal rod securing systems which require the use of tightening instrumentation oriented at an angle to the wound site. A pin 20, in the form of a set screw with an internal hexagonal wrench receiving surface 22, e.g., to accommodate an allen wrench, and an enlarged head 24 is threaded into each bore 18 from the bottom to complete the system.

The rod receiving grooves 14 are generally semicylindrical in shape with a radius slightly greater than the radius of the spinal rod 26 to be clamped within the groove to accommodate manufacturing and assembly tolerances. See FIG. 4. The enlarged head 24 of each clamping screw 20 has an outwardly and downwardly inclined or beveled surface 24a which may be formed as a straight, i.e., conical, surface as is illustrated in FIGS. 1 and 4 or with a concave surface 24b on the lower end thereof having a radius also slightly greater than the radius of the rod as is shown in FIG. 5.

Figure 3:
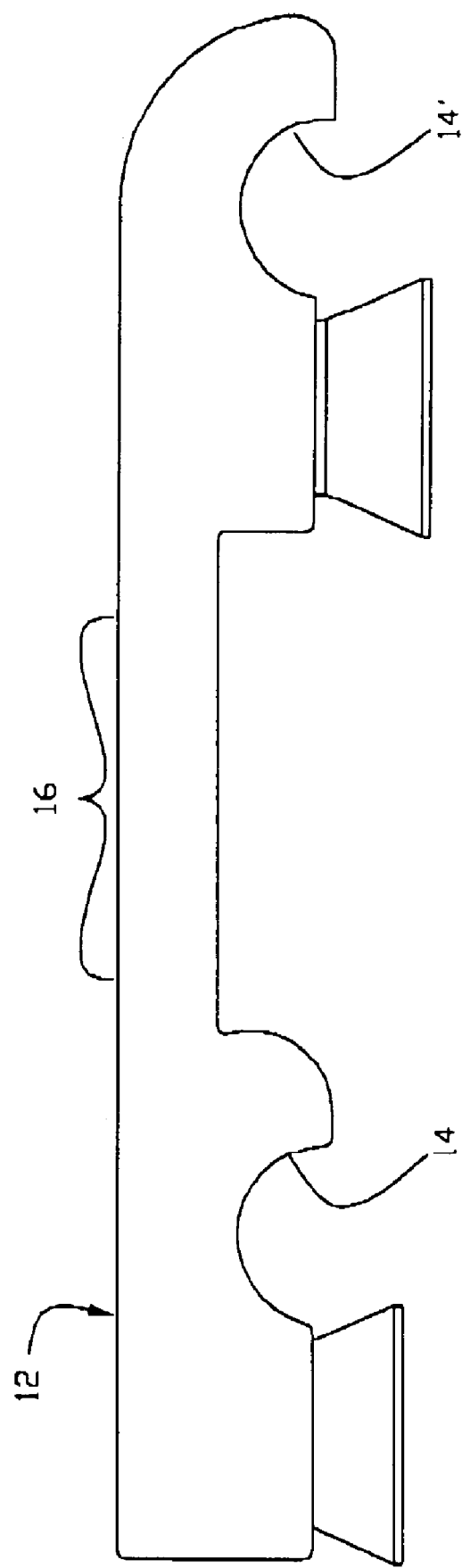
FIG. 3 is a side elevational view of a modified connector system in which one of the rod receiving grooves is located remote from the center section.

It is to be noted that one or both of the rod grooves may be located on the exterior side of the elongated members, i.e., remote from the bridge section 16, indicated at 14' in FIG. 3.

Figure 4:
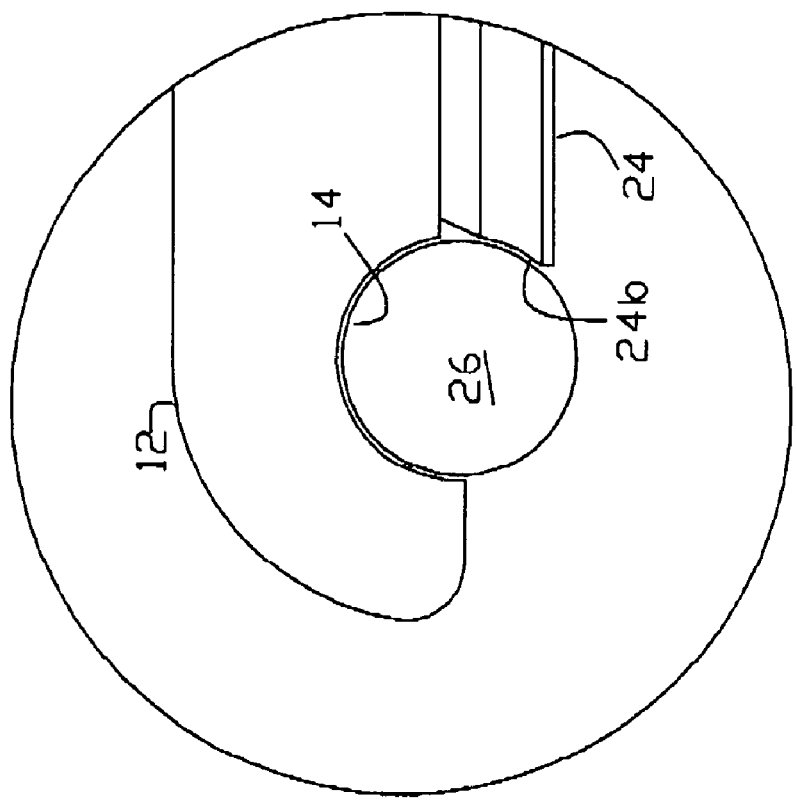
FIGS. 4 and 5 are side elevational views, partially broken away, of the assembly of FIG. 2 showing the path of the spinal rod into and captured within the rod receiving groove in the connector.

Prior to placement of the connector in the patient, the set screws 24 are in their lowered position, as is illustrated in FIGS. 1 and 4, leaving ample room for the placement of the connector ends over the rods. The clearance $d_1$ between the terminal end 14a of the groove and the side 24a of the set screw 24, in its lowered position, is greater than the diameter of the spinal rod. This allows the connector end with its rod receiving groove to be inserted over or removed from the rod as is illustrated in FIG. 4.

Figure 5:
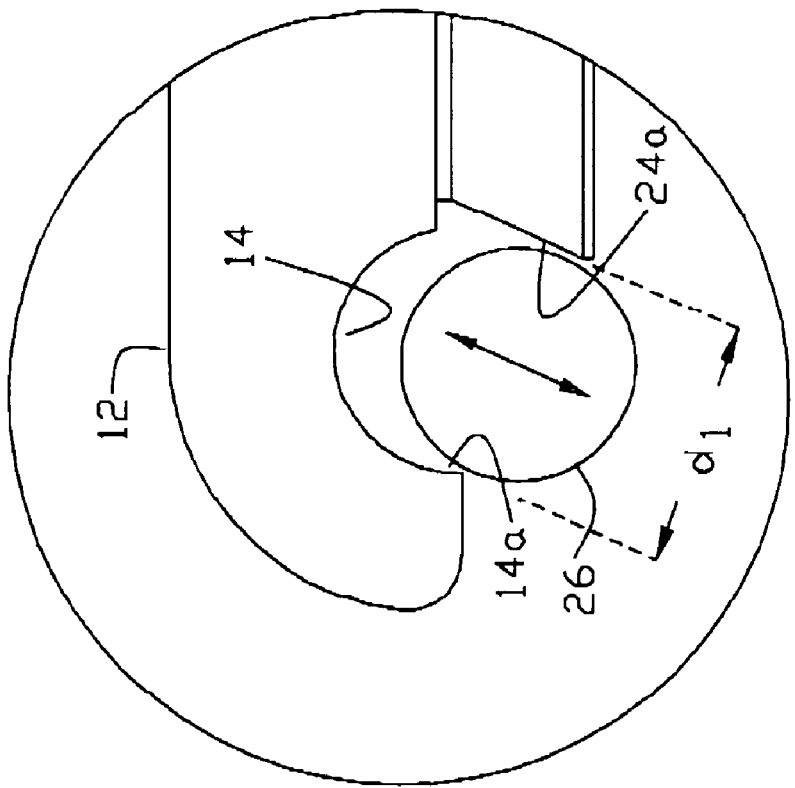
Figure 6:
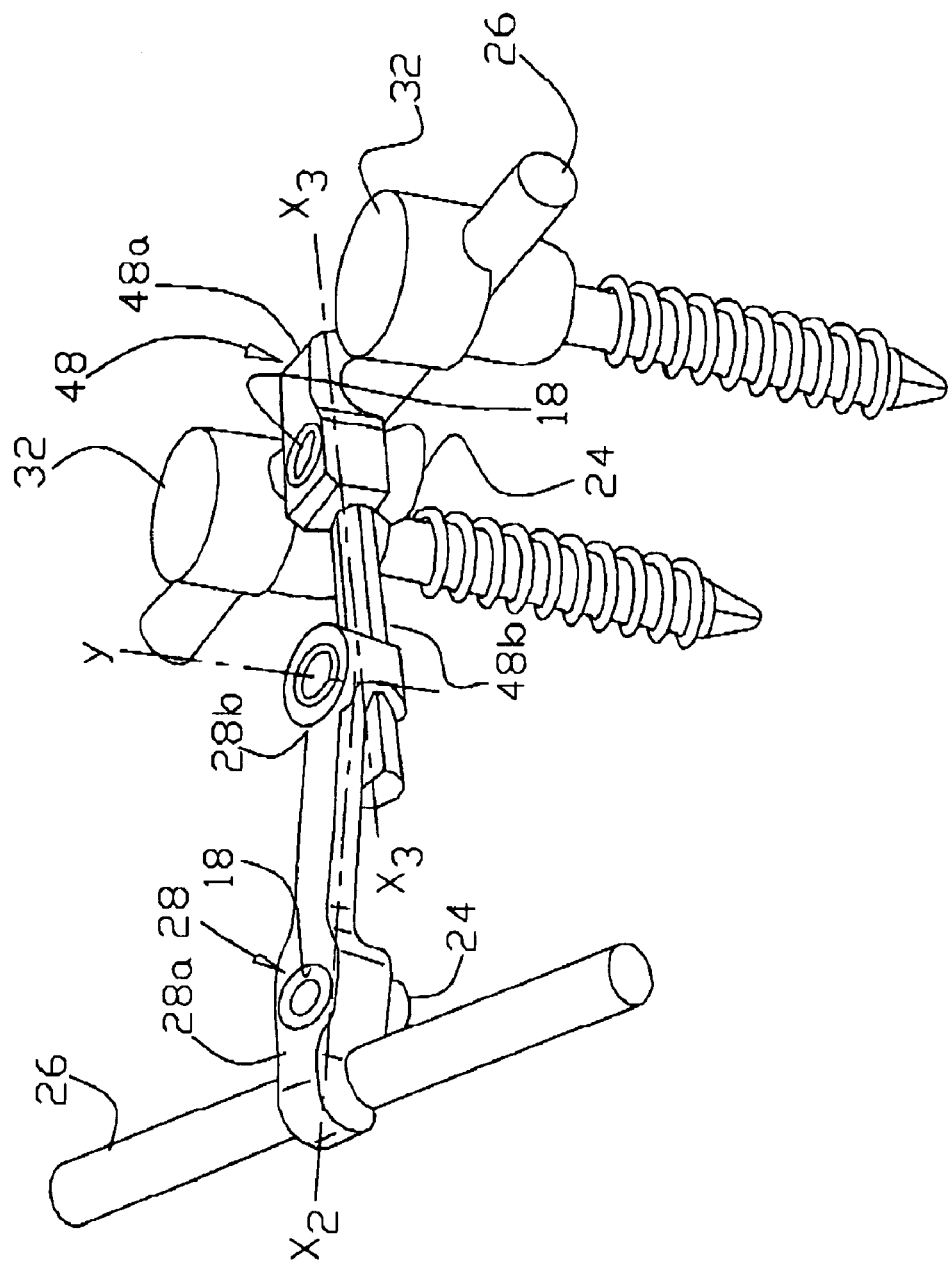
FIG. 6 is a perspective view of a universal transverse connector system in which the connector is formed of two members with one end of each member secured to a respective spinal rod and with two pedical screws depending from one of the rods.

If the rod is positioned at least part way into the groove, the set screw 24 may be retracted to force the connector end down to clamp the rod within the groove as is illustrated in FIG. 5. If the rod is fully seated within the groove the set screw may be retracted to complete the clamping action. With the set screw retracted the arc extending from the terminal end 14a of the groove to the side of the set screw 24 which contacts the side of the rod exceeds 180°.

During installation the surgeon will probably be required to bend and/or twist the bridge section 16 to provide the proper orientation between the connected spinal rods. It is to be noted that the connector may be formed of two or more elements which can be moved longitudinally, rotated and/or pivoted relative to each other to eliminate the necessity for the surgeon to bend and/or twist a portion of the connector to accommodate the desired spatial orientation of the rods.

A preferred universal or variable connector is illustrated in FIGS. 6–13 in which the connector includes first and second elongated members designated 28 and 48, respectively, connected between spinal rods 26. Pedical screws 32 (for insertion into the selected vertebrae not shown) are secured to one of the spinal rods for illustrative purposes. The elongated members 28 and 48 define longitudinal axis $X_2$ and $X_3$ respectively. Each member has a rod receiving groove 14 at a proximal end 28a or 48a thereof and a threaded pin/set screw receiving bore 18 adjacent thereto. As described with respect to FIGS. 2 and 3, the bores 18 are oriented at 90° with respect to the respective longitudinal axis and the top surfaces of the proximal ends as shown. It is to be noted that while the retractable clamping screw arrangement of FIGS. 1 and 2 is preferred as the means to secure the spinal rods in the embodiment of FIGS. 6–13, a more conventional clamping system, such as those disclosed in the prior art, could be used for this variable connector system.

Referring now to FIGS. 6–11, the distal end 28b of the first member 28 is formed with an upwardly facing serrated surface 34 substantially surrounding a threaded locking screw bore 36 as is shown in FIG. 8. A middle coupler 40, in the form of a ring, includes an upper section 40a which is mounted on the distal end of the first member in the assembled condition with a cylindrical opening 40b aligned, i.e., in registration with, but having a slightly larger diameter $d_2$ than the diameter of the head of a locking screw 42 to be described. See FIGS. 10 and 11.

A downwardly facing annular flat surface 40c of the coupler is arranged to engage the upwardly facing serrated surface 34 at the distal end of the first member when the system is in its locked position as will be explained in more detail. The serrated surface 34 tends to bite into the coupler surface 40c to inhibit any relative rotation between the coupler and first member in the locked position. In the unlocked position the coupler is free to rotate through a limited angle, e.g., +/−30°, relative to the distal end of the first member.

Figure 9:
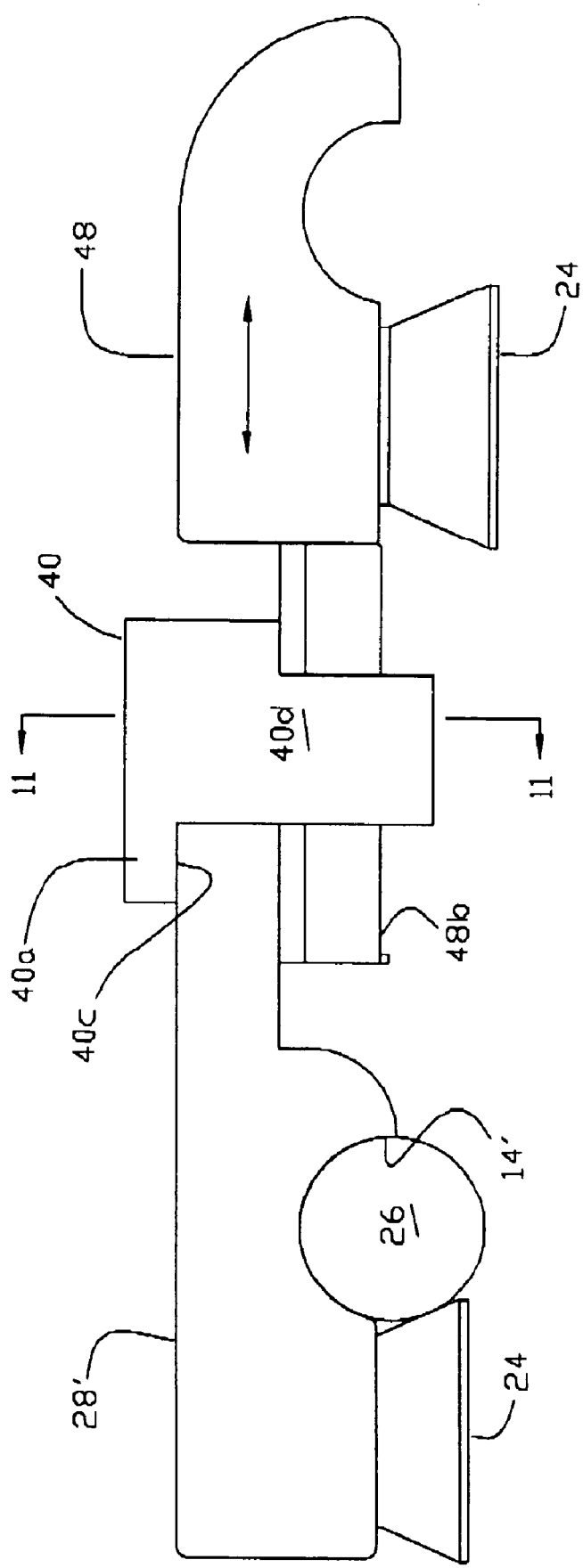
FIG. 9 is a side elevational assembled view of a modified connector system showing an alternative placement of a rod receiving groove in one of the members and also showing a spinal rod captured in that groove.

Instead of locating the rod receiving grooves on the interior side of the elongated members 48 and 28 as shown in FIGS. 7 and 8, one or both of the grooves may be located on the exterior side of the elongated member, i.e., near the distal end or remote from the coupler as is indicated at 14' in FIG. 9. This arrangement would allow the rod receiving grooves to slide as closely together as dimensionally allowed while preserving the ability of the system to accommodate various spatial orientations of the spinal rods.

The coupler is mounted on the distal end of the first member by means of a locking set screw 42, preferably having an enlarged head 42a seated within the opening 36. The set screw has a threaded shaft 42b which is received in the locking screw opening 36. See FIGS. 12 and 13. A generally u-shaped lower section 40d of the coupler terminates in a partial cylindrical or saddle-shaped (i.e., radiused) interior surface 40e and defines an opening 46 with the bottom surface of the distal end of the first member. The distal end 48b of the second elongated member 48 extends through this opening in the assembled condition.

The distal end 48b of the second member may have a cylindrical cross section with a corresponding opening 46 in the coupler, but preferably the distal end 48b has a cross section in the form of a lower rounded surface 48c (matching the curved surface 40e) with two substantially straight sides 48d terminating in a rounded or radiused crown 48e. The crown 48e preferably has a radius concentric to the radius of the surface 40e. The latter configuration allows for a reduced height profile while preserving the bending stiffness in the plane of the spinal rods.

In the assembled condition, before the locking screw is tightened, the second elongated member is free to move longitudinally and/or rotate about its axis $X_3$ relative to the first member. See FIGS. 6, 9, 12 and 13. The second member is also free to pivot through a limited angle about an axis Y perpendicular to the longitudinal axis $X_1$, via the coupler. See FIG. 6. The three degrees of freedom facilitate the surgeon's ability to accommodate normal spatial orientations of the spinal rods.

Figure 13:
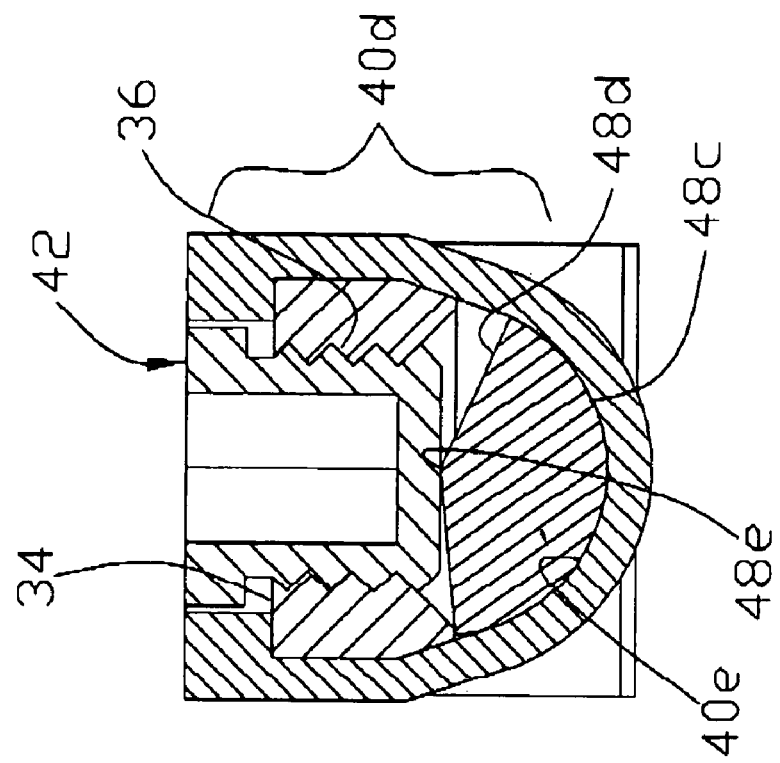
FIGS. 12 and 13 are cross-sectional views taken along line 11—11 of FIG. 9 demonstrating the rotation of the second member about its longitudinal axis relative to the first member.
Figure 12:
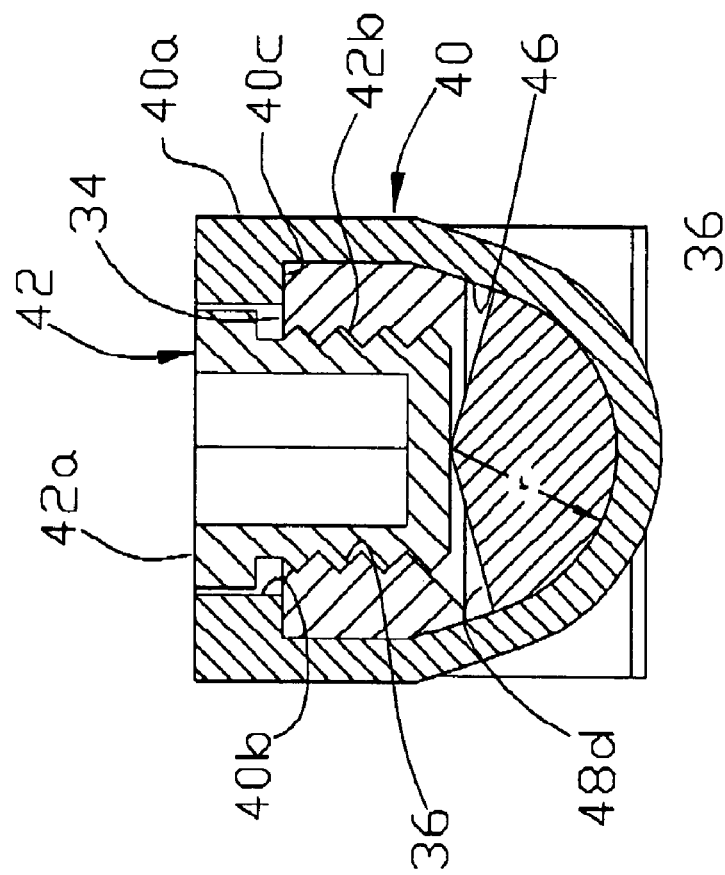

During installation the rod receiving grooves of the system may be positioned angularly with respect to each other and moved towards or away from each other. Once the clamping set screws are retracted to lock the assembly to the rods, the connector assembly may then be locked in a fixed position by advancing the locking set screw to force the portion of the distal end of the second member within the coupler downwardly to clamp it between the end of the set screw and the coupler internal surface 40e. This action also forces the distal end of the first member upwardly to lock the surfaces 40c and 34 together as is illustrated in FIGS. 12 and 13.

The component parts of the connector system may be made of any high strength materials, such as medical grade steel or titanium compound, suitable for implantation into the human body.

By way of example, the first and second elongated members may have a length and width of about 1" and ¼", respectively.

The transverse connector system described and illustrated provides a minimum disturbance of the area underlying the spinal rods while accommodating the use of a single instrument or wrench extending directly out of the wound site to secure the system to the rods. An additional advantage is achieved by forming the connector in two separate members with a middle coupler and locking screw for locking the elements together in a desired spatial orientation.

Various modifications of the invention will occur to those skilled in the art without involving any departure from the spirit and scope of the invention as called for in the appended claims.

What is claimed is:

1. A variable transverse connector system for rigidly joining together first and second spinal rods at a desired spatial orientation comprising:
    first and second elongated members with each member defining a longitudinal axis, a proximal and distal end, the distal end of the first member having a locking screw receiving threaded bore extending there through;
    means for securing the proximal ends of the first and second elongated members to a respective spinal rod,
    a coupler adapted to be mounted on the distal end of the first member for limited pivotal movement about an axis perpendicular to the longitudinal axis of the first member, the coupler having an upper section arranged to fit over the distal end of the first member with a cylindrical opening aligned with the threaded bore in the distal end of the first member, and a lower section defining an internal curved surface for receiving the distal end of the second member to accommodate movement of the second member along and rotation about its longitudinal axis relative to the first member; and
    a locking screw adapted to be inserted into the locking screw receiving bore for engagement with the distal end of the second member to lock the first and second members together whereby the spinal rods are joined together at the desired spatial orientation.

2. The transverse connector of claim 1 wherein the securing means comprises a rod receiving groove on the proximal end of each elongated member, a pin receiving bore adjacent the rod receiving groove, and a clamping pin arranged for translational movement within each pin receiving bore, and further wherein the clamping pins are set screws.

3. The connector of claim 2 wherein the pin receiving bores are vertically oriented when the elongated members are horizontal.

4. The connector of claim 2 wherein the clamping pins are arranged to be retracted to clamp the spinal rods into a respective rod receiving groove.

5. The connector system of claim 2 wherein the pin receiving bores are threaded and the pins include a threaded shaft portion positioned within their associated bores and an enlarged head portion positioned below the bores, each head portion being arranged to engage a side of a respective rod when the pin is retracted to clamp the rod within the groove, the pin and head portion forming a single unitary piece.

6. The connector system of claim 5 wherein the enlarged head portions are beveled outwardly and downwardly.

7. The connector system of claim 6 wherein the bevel includes a concave portion adapted to engage the side of a respective rod.

8. The connector system of claim 5 wherein the rod receiving groove and the engagement of the beveled head portion of the set screw form an arc encompassing more than 180°.

9. The connector system of claim 5 wherein the set screws and pin receiving bores are reverse threaded whereby a clockwise rotation of the set screw retracts the screw.

10. The connector system of claim 5 wherein each of the elongated members has an exterior side remote from the coupler and an interior side close to the coupler and wherein the rod receiving grooves are located on the interior side of the elongated members.

11. The connector system of claim 5 wherein one of the rod receiving grooves is located on the exterior side of the respective elongated member and the other rod receiving groove is located on the interior side of the respective elongated member.

12. The transverse connector of claim 1 wherein the lower section of the coupler defines a generally semicylindrical internal surface having a radius r and the distal end of the second member has a complementary lower curved surface with about the same radius.

13. The transverse connector of claim 12 wherein the distal end of the second member has an upper section with generally straight sides extending from the lower curved surface to a radiused crown adapted to be engaged by the locking screw.

14. The transverse connector of claim 13 wherein the crown is formed with a radius approximately concentric to r.

15. The connector system of claim 1 wherein the coupler defines a downwardly facing flat surface surrounding the cylindrical opening thereon and the distal end of the first member defines an upwardly facing flat surface surrounding the threaded bore, the locking screw being arranged to force the distal end of the second member downwardly against the coupler's internal curved surface while at the same time forcing the upwardly facing surface of the distal end of the first member against the downwardly facing surface of the coupler to lock the members together.

16. A variable transverse connector system for rigidly joining together first and second spinal rods at a desired spatial orientation comprising:

first and second elongated members with each member defining a longitudinal axis, a proximal and distal end, the distal end of the first elongated member defining a threaded opening therein;

means for securing the proximal ends of the elongated members to a respective rod;

a coupler mounted on the distal end of the first member for limited pivotal movement about an axis perpendicular to the longitudinal axis of the first elongated member, the coupler having an upper section defining a cylindrical opening positioned over and aligned with, but having a larger diameter than the opening in the distal end of the first elongated member, the coupler having a lower section defining an opening through which the distal end of the second elongated member extends allowing the second elongated member to move along and rotate about its longitudinal axis relative to the first member; and a locking set screw having a cylindrical head rotatably positioned within the cylindrical opening in the coupler and a shaft threaded into the opening in the distal end of the first member for releasably locking the distal ends of the elongated members together to join the rods at the desired spatial orientation.

17. The connector system of claim 16 wherein the securing means comprises a rod receiving groove on the proximal end of each elongated member, a pin receiving bore adjacent the rod receiving groove and a clamping pin arranged for translational movement within each pin receiving bore, and further wherein the clamping pins are set screws.

18. The connector system of claim 16 wherein the lower section of the coupler defines a radiused interior surface and wherein the distal end of the first member defines an upwardly facing serrated surface extending around the threaded bore therein and wherein the coupler defines a downwardly facing surface surrounding the opening therein whereby advancement of the set screw forces the distal end of the second member against the radiused interior surface and the serrated distal end of the first member against the downwardly facing surface of the coupler to lock the distal ends of the members together.

19. The connector system of claim 16 wherein the rod receiving grooves are located on the exterior side of the elongated members.

* * * * *